US008192787B2

(12) United States Patent
Kirby

(10) Patent No.: US 8,192,787 B2
(45) Date of Patent: Jun. 5, 2012

(54) METHOD OF PRODUCING A MICRONEEDLE OR MICROIMPLANT

(75) Inventor: Andrew James Kirby, Cyncoed (GB)

(73) Assignee: Innoture Limited, Cardiff (GB)

( * ) Notice: Subject to any disclaimer, the term of this patent is extended or adjusted under 35 U.S.C. 154(b) by 1013 days.

(21) Appl. No.: 11/660,341

(22) PCT Filed: Aug. 16, 2005

(86) PCT No.: PCT/GB2005/003224
§ 371 (c)(1),
(2), (4) Date: Dec. 4, 2007

(87) PCT Pub. No.: WO2006/018642
PCT Pub. Date: Feb. 23, 2006

(65) Prior Publication Data
US 2008/0299290 A1 Dec. 4, 2008

(30) Foreign Application Priority Data

Aug. 16, 2004 (GB) ................................ 0418246.5
Dec. 17, 2004 (GB) ................................ 0427762.0

(51) Int. Cl.
B05D 1/36 (2006.01)
(52) U.S. Cl. .................. 427/2.28; 604/187; 604/272
(58) Field of Classification Search ............... 427/2.28; 604/187, 272
See application file for complete search history.

(56) References Cited

U.S. PATENT DOCUMENTS

| | | | |
|---|---|---|---|
| 3,964,482 A | 6/1976 | Gerstel et al. | |
| 5,309,909 A | 5/1994 | Gadsby et al. | |
| 6,440,096 B1 | 8/2002 | Lastovich et al. | |
| 6,558,361 B1 | 5/2003 | Yeshurun | |
| 6,743,211 B1 | 6/2004 | Prausnitz et al. | |
| 2002/0020688 A1 | 2/2002 | Sherman et al. | |
| 2002/0042589 A1 | 4/2002 | Marsoner | |
| 2002/0169411 A1 | 11/2002 | Sherman et al. | |
| 2003/0135201 A1 | 7/2003 | Gonnelli | |
| 2003/0187394 A1 | 10/2003 | Wilkinson et al. | |
| 2003/0187395 A1 | 10/2003 | Gabel et al. | |
| 2004/0072105 A1 * | 4/2004 | Yeshurun et al. ............ | 430/313 |
| 2004/0260251 A1 | 12/2004 | Chang et al. | |
| 2006/0127465 A1 | 6/2006 | Maenosono et al. | |
| 2006/0163215 A1 | 7/2006 | Maenosono et al. | |

FOREIGN PATENT DOCUMENTS

| | | |
|---|---|---|
| EP | 1 086 718 A1 | 3/2001 |
| JP | 54-028369 | 3/1979 |
| JP | 2003-238347 | 8/2003 |
| WO | WO 99/64580 | 12/1999 |
| WO | WO 00/67647 | 11/2000 |
| WO | WO 00/74763 A2 | 12/2000 |
| WO | WO 00/74764 A1 | 12/2000 |
| WO | WO 00/74766 A1 | 12/2000 |
| WO | WO 01/36036 A1 | 5/2001 |
| WO | WO 01/49346 A1 | 5/2001 |
| WO | WO 01/49346 A3 | 5/2001 |
| WO | WO 01/66065 A2 | 9/2001 |
| WO | WO 01/66065 A3 | 9/2001 |
| WO | WO 01/91846 A2 | 12/2001 |
| WO | WO 01/91846 A3 | 12/2001 |
| WO | WO 01/93930 A1 | 12/2001 |
| WO | WO 02/02179 A1 | 1/2002 |
| WO | WO 02/15960 A2 | 2/2002 |
| WO | WO 02/15960 A3 | 2/2002 |
| WO | WO 02/17985 A2 | 3/2002 |
| WO | WO 02/17985 A3 | 3/2002 |
| WO | WO 02/45771 A3 | 6/2002 |
| WO | WO 02/49507 A1 | 6/2002 |
| WO | WO 02/50584 A2 | 6/2002 |
| WO | WO 02/50584 A3 | 6/2002 |
| WO | WO 02/064193 A2 | 8/2002 |
| WO | WO 02/064193 A3 | 8/2002 |
| WO | WO 02/072189 A2 | 9/2002 |
| WO | WO 02/072189 A3 | 9/2002 |
| WO | WO 02/091922 A1 | 11/2002 |
| WO | WO 02/100459 A2 | 12/2002 |
| WO | WO 02/100459 A3 | 12/2002 |
| WO | WO 02/100474 A2 | 12/2002 |
| WO | WO 02/100474 A3 | 12/2002 |
| WO | WO 03/020359 A2 | 3/2003 |
| WO | WO 03/020359 A3 | 3/2003 |
| WO | WO 03/024507 A2 | 3/2003 |
| WO | WO 03/024507 A3 | 3/2003 |
| WO | WO 03/024508 A2 | 3/2003 |
| WO | WO 03/024508 A3 | 3/2003 |
| WO | WO 03/026732 A2 | 4/2003 |
| WO | WO 03/026732 A3 | 4/2003 |
| WO | WO 03/026733 A2 | 4/2003 |
| WO | WO 03/026733 A3 | 4/2003 |

(Continued)

OTHER PUBLICATIONS

Martanto et al., "Transdermal delivery of insulin using microneedles in Vivo," *Pharmaceutical Research* (2004) 21 (6): 947-952.

(Continued)

*Primary Examiner* — Peter Szekely
(74) *Attorney, Agent, or Firm* — Merchant & Gould P.C.

(57) ABSTRACT

A method of manufacturing microneedles is provided, the method includes (i) depositing a substance onto a first surface and (ii) forming a solid needle-like shape from the substance. The substance may be deposited in non-solid form and subsequently solidified. A method provides an array of such microneedles.

16 Claims, 4 Drawing Sheets

FOREIGN PATENT DOCUMENTS

| | | | |
|---|---|---|---|
| WO | WO 03/037403 | A1 | 5/2003 |
| WO | WO 03/037404 | A1 | 5/2003 |
| WO | WO 03/059431 | A1 | 7/2003 |
| WO | WO 03/061636 | A2 | 7/2003 |
| WO | WO 03/061636 | A3 | 7/2003 |
| WO | WO 03/061731 | A2 | 7/2003 |
| WO | WO 03/061731 | A3 | 7/2003 |
| WO | WO 03/066128 | A2 | 8/2003 |
| WO | WO 03/066128 | A3 | 8/2003 |
| WO | WO 03/084598 | A1 | 10/2003 |
| WO | WO 2004/009172 | A1 | 1/2004 |
| WO | WO 2004/021882 | A2 | 3/2004 |
| WO | WO 2004/021882 | A3 | 3/2004 |
| WO | WO 2004/022138 | A2 | 3/2004 |
| WO | WO 2004/022138 | A3 | 3/2004 |
| WO | WO 2004/033021 | A1 | 4/2004 |
| WO | WO 2004/035105 | | 4/2004 |
| WO | WO 2004/035105 | A2 | 4/2004 |
| WO | WO 2004/035105 | A3 | 4/2004 |
| WO | WO 2004/062899 | A2 | 7/2004 |
| WO | WO 2004/064889 | A2 | 8/2004 |
| WO | WO 2004/064889 | A3 | 8/2004 |
| WO | WO 2004/007597 | A1 | 9/2004 |
| WO | WO 2004/075971 | A1 | 9/2004 |
| WO | WO 2004/108203 | | 12/2004 |

OTHER PUBLICATIONS

Prausnitz et al., "Current status and future potential of transdermal drug delivery," *Nature Reviews* (2004) 3: 115-124.

\* cited by examiner

METHOD OF PRODUCING A MICRONEEDLE OR MICROIMPLANT

The present invention relates to a method of producing small-scale structures, in particular microneedles or microimplants, particularly but not exclusively for use in the pharmaceutical industry.

Transdermal drug delivery is an important route for pharmaceutical actives, but the outer layer of skin, the 10-20 micrometer thick layer called the stratum corneum, is an effective barrier for many chemical entities. Hence, the number of pharmaceutically active materials that can penetrate into the body through the skin is very limited, and is defined by factors such as polarity, log P, and molecular size. At the same time, many drugs are being synthesized which are unsuitable for oral delivery (for example, due to instability in the gastrointestinal tract, or first pass liver metabolism). Hence, the skin is an attractive, if problematic, route for delivery of these drugs, as well as drugs that act in the skin, but perhaps have systemic side effects.

Several methods have been developed in order to compromise the skin barrier function to allow penetration of drugs into, and analytes out of (for monitoring purposes), the body. These include sonophoresis, iontophoresis and microneedles. U.S. Pat. No. 3,964,482 describes the use of microneedles to assist in the delivery of drugs across the skin. Microneedles puncture the stratum corneum, allowing passage of drug into the subject, but preferably do not induce a pain response because the microneedles do not penetrate to the dermal layer of the skin which is provided with nerve cells.

Several methods have been proposed for the manufacture of microneedles. U.S. Pat. No. 6,558,361 discloses the use of photolithography to produce microneedles. WO2004/062899 discloses the formation of microneedles using a mould. Other needle and master fabrication methods include etching techniques, thermal oxidation of silicon, Liga, stereolithography, laser machining and laser ablation.

Such methods are typically time consuming and require expensive facilities to fabricate microneedles. Moulding, for example, presents other problems, such as the quality of the microneedles being limited by the quality of the master and the lifetime of the mould. Furthermore, moulds present problems in the event that the needles are of a high aspect ratio; such moulds may be difficult to fill and may not be released readily from the microneedles formed by the mould. The present invention seeks to mitigate at least one or more of the problems of the prior art.

In accordance with a first aspect of the present invention there is provided a method of manufacturing microneedles or microimplants, the method comprising
(i) depositing a substance onto a first surface and
(ii) forming a solid needle-like shape from the substance.

This provides an effective and generally inexpensive method for producing microneedles.

Step (i) may comprise depositing a first-portion or droplet of substance onto the first surface. This facilitates, for example, the sequential deposition of portions or droplets to produce microneedles, or needle-like structures to be drawn from a portion or droplet. As an alternative to the deposition of discrete portions or droplets, a contiguous film or layer of substance may be deposited onto the first surface.

The first surface is preferably a solid surface, but may be a non-solid surface.

Step (i) may comprise depositing the substance in non-solid form. Such a non-solid substance may flow or be flowable.

The substance in its non-solid form may, for example, be in the form of a liquid, gel, emulsion, cream, paste or thixotropic material. It should be noted that the substance in non-solid form may comprise solids, for example, in the form of particles. These particles may be suspended or dispersed in a carrier so that the bulk substance is non-solid.

Step (i) may comprise depositing the substance in solid form. Such substances may not flow. An example of such a step may include the deposition of a solid substance by laser printing.

In the event that the substance is deposited on the first surface in non-solid form, then the step of forming a solid from the substance may, for example, include exposure of the substance to ultraviolet radiation to form a solid polymer, loss of solvent to form a solid and curing over time (for example, when the non-solid substance comprises a two-part epoxy resin that, over time, cures to form a solid). The solid needle-like structure may not (and more probably, will not) have the same chemical composition as the non-solid substance.

Step (ii) may comprise depositing a second portion or droplet of substance onto the first portion or droplet of substance. This allows a needle-like structure to be built-up by depositing one portion of substance upon another. It further allows fast production of needle-like structures using automatic liquid deposition technology.

If the first portion or droplet is deposited in non-solid form, then it is preferred that the first portion or droplet is at least partially solidified prior to the deposition of the second or droplet of substance. Partially solidifying the first portion or droplet of substance may include exposing the first portion or droplet to electromagnetic radiation, for example, or merely waiting for a pre-determined time period before depositing the second portion or droplet.

One or both of the first and second portions of substance may be deposited in solid form. This would facilitate the production of microneedles using certain printing techniques, such as laser printing.

It is preferred that the volume of the second droplet or portion is smaller than the volume of the first droplet or portion. This facilitates the production of needle-like structures.

Needle-like structures may be built-up by the sequential deposition of droplets or portions of substance on top of each other.

Step (ii) may comprise sequential deposition of a plurality of portions or droplets of substance onto the first portion or droplet. If one or more of the portions or droplets is deposited in non-solid form, then it is preferred that the said one or more portion or droplet is at least partially solidified prior to the deposition of a further portion or droplet of substance thereon. If one or more of the portions or droplets is deposited in non-solid form, then it is preferred that each of the portions or droplets is deposited in non-solid form. This facilitates the production of needle-like shapes. In this case, it is preferred that the volume of the further portion or droplet is smaller than the volume of the immediately underlying portion or droplet at deposition of the immediately underlying portion or droplet.

In addition, or as an alternative, to the sequential deposition of droplets or portions as described above, step (ii) may comprise providing a second surface that is in contact with the (preferably non-solid) substance and moving the first surface and the second surface relative to one another to form a needle-like shape. This drawing of needles is especially of benefit when the substance is in non-solid form. Drawing of needles is relatively simple to achieve and further lends itself to being a rapid and automated process. For example, the method of the present invention may comprise depositing one or more portions of substance using the sequential deposition method as described above and then drawing a needle-like shape from the said substance.

Step (i) may comprise providing a portion or droplet of non-solid substance on the second surface, and moving the second surface into proximity to the first surface so that the droplet or portion of non-solid substance contacts the first surface. Providing a portion or droplet of non-solid substance on the second surface may be achieved, for example, by providing the non-solid substance in a reservoir and contacting the second surface with the non-solid substance in the reservoir. This allows the second surface to pick-up the substance from a reservoir and deposit it onto the first surface prior to the drawing of the needle. Alternatively, the second surface may be associated with an aperture or bore through which the non-solid substance is passed so as to deposit the substance (possibly as a discrete portion or droplet) onto the second surface.

Alternatively, step (i) may comprise depositing the non-solid substance onto the first surface in the absence of the second surface. The non-solid substance may be deposited in the form of a droplet or portion, or as a contiguous film or layer.

As a further alternative, step (i) may comprise bringing the second surface into proximity to the first surface and subsequently providing the non-solid substance on the first surface so as to form a contact between the non-solid substance and the second surface. This could be achieved by introducing the substance through an aperture provided in or proximate to the first surface or an aperture provided in or proximate to the second surface.

The second surface may be provided by a solid or a liquid.

When the method of the present invention comprises moving the second surface in relation to the first surface, step (ii) may comprise the sequential steps of (a) moving the first surface and the second surface relative to one another to form a needle-like shape and (b) forming a solid needle-like shape. Contact may be maintained between the substance and the second surface during the formation of the solid needle-like shape. Alternatively, the second surface may be removed from the substance after step (a) and prior to step (b).

Step (ii) may comprise forming a solid needle-like shape while moving the first surface and the second surface relative to one another.

The deposition of the substance may be achieved using a printing method, such as stencil based deposition, contact printing (for example pin transfer) and other printing methods such as gravure, offset, electronic printing including xerographic and laser printing, inkjet or bubble printing, flexography, magnetography, and direct charge deposition. Such methods may conveniently be used to deposit a first portion or droplet of substance (in solid or non-solid form). They may conveniently be used to sequentially deposit a plurality of portions or droplets one upon another so as to form a needle-like shape.

If the droplets or portions are deposited in non-solid form, then it is preferred that a portion or droplet is at least partially solidified prior to the deposition of a further portion or droplet of substance thereon.

Step (i) may comprise providing a stencil comprising at least one aperture, and depositing the substance (preferably in non-solid form) through the at least one aperture onto the first surface. Depositing the substance (preferably in non-solid form) through the at least one aperture may be achieved by urging the substance into the at least one aperture (as opposed to allowing the substance to spontaneously pass through the at least one aperture). This may be achieved, for example, by depositing the substance on the stencil and wiping the substance across the stencil and across the at least one aperture.

Step (ii) may comprise moving the stencil in relation to the first surface, thus forming a needle-like shape. In this way, the stencil is acting like the second surface referred to above. The needle-like shape may be solidified as described elsewhere herein.

Alternatively, step (ii) may comprise moving the stencil in relation to the first surface, approximating the first surface to a second surface so that the second surface contacts the substance, and moving the second surface in relation to the first surface so as to form a needle-like shape.

Step (ii) may comprise providing a stencil comprising at least one aperture, and depositing a plurality of portions or droplets of substance in (preferably in non-solid form) through the at least one aperture of the stencil. If a portion or droplet is deposited in non-solid form, then it is preferred that said portion or droplet is at least partially solidified prior to the deposition of a further portion or droplet of substance thereon. This may be achieved, for example, by depositing substance in non-solid form on the stencil, wiping the substance over the at least one aperture, moving the stencil and the first surface away from one another, solidifying the substance, approximating the stencil to the first surface, and then wiping substance in non-solid form over the at least one aperture.

The deposition of a portion or droplet of substance may be performed by one or more of ink-jet printing, screen printing or micropipetting. Such methods may conveniently be used to produce microneedles and arrays of micro-needles quickly.

The deposition of the substance (and preferably a portion or droplet of non-solid substance) may be by an automated handling system. The automated handling system may employ one or more of piezo valves, solenoid valves, syringe pumps, microelectromechanical devices, or air or other gas displacement means. These represent convenient means of controlling the deposition of the substance, especially if the substance is to be deposited in portions or droplets.

The deposition of the substance may be by microarrayer or another automated contact printing device. These represent convenient means of controlling the deposition of the substance, especially if the substance is to be deposited in portions or droplets.

The first surface may be part of, or a precursor to, a transdermal patch.

The solid, needle-like shape may comprise one or both of an organic or silicone polymer, including epoxy resins, acrylic polymers and silicone resins.

Alternatively or additionally, the solid needle-like shape may comprise a metal, such as titanium. The solid needle-like shape may comprise a mixture of a metal and non-metals (such as silica). The needle may comprise silicon (for example, porous silicon), a ceramic or a mineral.

The solid needle-like shape may comprise silica.

Further preferred materials include UV curable plastics such as acrylates, urethane acrylates and bioresorbable or biodegradable materials such as polylactides. Combinations of any materials can be used to form the needle. For instance, the base of a needle could be made of acrylate polymers, with one or more different strata of other materials, such as polylactides, or materials with particular characteristics such as ease of breakage to allow the tip of a needle to remain in the organism.

The method may comprise inserting an elongate former into the substance prior to solidification so as to form a groove or bore in the needle-like shape. Such a groove may be useful for delivering fluids through the needle into the subject or article into which the needle may be inserted.

The solid needle-like shape may be porous. A porous needle may be formed, for example, by one or more of causing a gas to pass through the needle-like shape during its formation; by providing a substance that spontaneously forms a solid, needle-like shape having a porous structure; by providing the substance with a component that may be removed (by dissolution, combustion or otherwise) from the solid, needle-like shape and by providing a substance that, on formation of a solid, needle-like shape, forms a porous mesh of fibres. Such porosity may be useful for delivering fluids through the needle into the subject or article into which the needle may be inserted.

The method may further comprise introducing a dopant into the substance in order for the dopant to be released from the resultant solid at a later time.

Step (i) or (ii) may comprise deposition of a catalyst or other reaction promoter. For example, a catalyst for curing the substance could be deposited first on to the first surface, and the substance in non-solid form deposited on top of the catalyst. The catalyst would start to cure the substance on contact.

The needle-like shape may be wholly or partly biodegradable.

The needle-like shape may be readily separable from the first surface. This may facilitate the transfer of the needle from the first surface to a further surface. It may be desirable for the needle-like shape to be readily detachable in use.

The solid, needle-like shape may be readily breakable to yield a first portion associated with the first surface and a second, dissociated portion.

The step of forming a solid needle-like shape from a non-solid substance may comprise one or more of cooling the substance, heating the substance, waiting for a given period or exposing the non-solid substance to electromagnetic radiation (typically ultraviolet radiation). Cooling the substance may cause the substance to spontaneously form a solid. Heating may drive-off solvent from the substance, therefore causing a solid needle-like shape to form. Exposing the substance to electromagnetic radiation may cause the formation of a solid, for example, in the event that the non-solid substance is in the form of a UV-curable resin or adhesive. Waiting for a given period may cause the formation of a solid if, for example, the substance in its non-solid form is a two-part epoxy resin.

The needles may be about 10 microns to 3 mm long, preferably greater than 100 microns long and more preferably less than 1 mm long. The most preferred length is about 200 to 400 microns. Such a length of projection minimizes the chance of a projection reaching the dermis which is provided with nerves which generate pain response. The preferred length may vary depending on the biological layer which is intended to be punctured by the projections. For example, mucosal layers may require projections of different length than the stratum corneum. Furthermore, if the microneedle is intended to puncture the stratum corneum of a human subject, then the preferred length of the microneedle may depend on the anatomical site at which the microneedle is intended to be used because the thickness of the stratum cornuem may vary between different anatomical sites.

It is most preferred that the microneedle is capable of puncturing a biological barrier, most preferably the stratum corneum of a human or animal. Furthermore, the method is preferably a method for forming a device for the puncturing of a biological barrier.

The first surface is preferably provided by a substrate that forms part of a transdermal patch. Alternatively, the first surface may be provided by paper, glass, plastic, an adhesive semipermeable dressing film, metal and the adhesive side of pressure sensitive adhesive tape.

The solid, needle-like structure may include a pharmaceutically active material. This may be achieved by introducing the pharmaceutically active material into the liquid prior to solidification or after solidification.

The first surface onto which the solid, needle-like shape of the present invention may be formed may be provided by pillars, protrusions or the like. The method of the present invention may therefore by used to make microneedles on existing, needle-like or protruding structures.

The solid needle-like shape may be conical. The solid needle-like shape may be pyramidal (for example, having three or four sides that converge to a point). The solid, needle-like shape may be curved. This may be achieved, for example, by using the needle-drawing method mentioned above and by moving the first and second surfaces relative to one another so as to produce a curved shape. The solid, needle-like shape may be provided with a hook, for example, by using the needle-drawing method mentioned above and by moving the first and second surfaces relative to one another so as to produce a hooked shape.

In accordance with a second aspect of the present invention there is provided a method of producing an array of microneedles, the method comprising:
(i) depositing a substance onto a first surface and
(ii) forming an array of solid needle-like shapes from the substance.

The method in accordance with the second aspect of the present invention preferably does not involve the use of a mould.

Step (i) may comprise depositing an array of first portions or droplets of substance onto a first surface.

Step (i) may comprise deposition of a substance in non-solid or solid form.

The production of an array of droplets or portions may be achieved by the serial deposition of droplets or portions on the first surface. Alternatively, an array of droplets or portions corresponding to the array of microneedles may be deposited simultaneously on the first surface.

Step (ii) may comprise depositing an array of second droplets or portions of substance onto the array of first droplets or portions of substance. An array of third portions or droplets may be deposited onto the array of second portions or droplets. As described above in relation to the production of just one microneedle, an array of needle-like structures may be developed by the sequential deposition of droplets or portions of substance. The method used in relation to the array may incorporate those features described above in relation to the method of the first aspect of the present invention.

The substance may be deposited in a non-solid form and step (ii) may comprise providing a second surface in contact with the substance and moving the first surface and the second surface relative to one another to form a needle-like shape. An array of needle-like structures may, therefore, be drawn from the substance as described above with reference to the first aspect of the present invention. This substance may be deposited as discrete portion or droplets, or as a contiguous film or layer. Step (ii) may comprise introducing an array of second surfaces into contact with the non-solid substance and drawing the substance into an array of needle-like shapes. Alternatively, the microneedle structures may be drawn from the array of droplets or portions by introducing a second surface into contact with the array of portions or droplets and drawing the array of droplets or portions into an array of needle-like shapes. This may be achieved using a single, substantially flat planar second surface.

Alternatively, one or more second surfaces may be used to sequentially draw needle-like shapes from the substance (optionally deposited as droplets or portions), the one or more second surfaces being moved so that the array of needles may be produced.

The method of the second aspect of the present invention may comprise those features described above with reference to the method of the first aspect of the present invention. For example, a stencil may be used to provide an array, as described with reference to the first aspect of the present invention.

In accordance with a third aspect of the present invention, there is provided a method of manufacturing microneedles or microimplants, either singly or in arrays, using deposition of a liquid onto a solid surface with subsequent or concurrent curing or other solidification into a solid needle-like shape, without use of a mould.

The method of the third aspect of the present invention may comprise those features described above with reference to the method of the first aspect of the present invention.

The present invention also provides a device for application to a biological barrier, the device comprising a substrate provided with one or more microneedle made in accordance with the method of the first, second or third aspects of the present invention. The device may comprise a first surface onto which one or more microneedle have been deposited using a method in accordance with the first, second or third aspects of the present invention. The first surface may be flexible. The device may, for example, be a transdermal patch. The device may comprise a sensor, a pump, or drug delivery device. The device may be provided with a means for urging the one or more microneedle into a biological barrier. The device may comprise a drug-eluting stent.

The invention will now be described by way of example only with reference to the following schematic figures of which:

Figure 1:
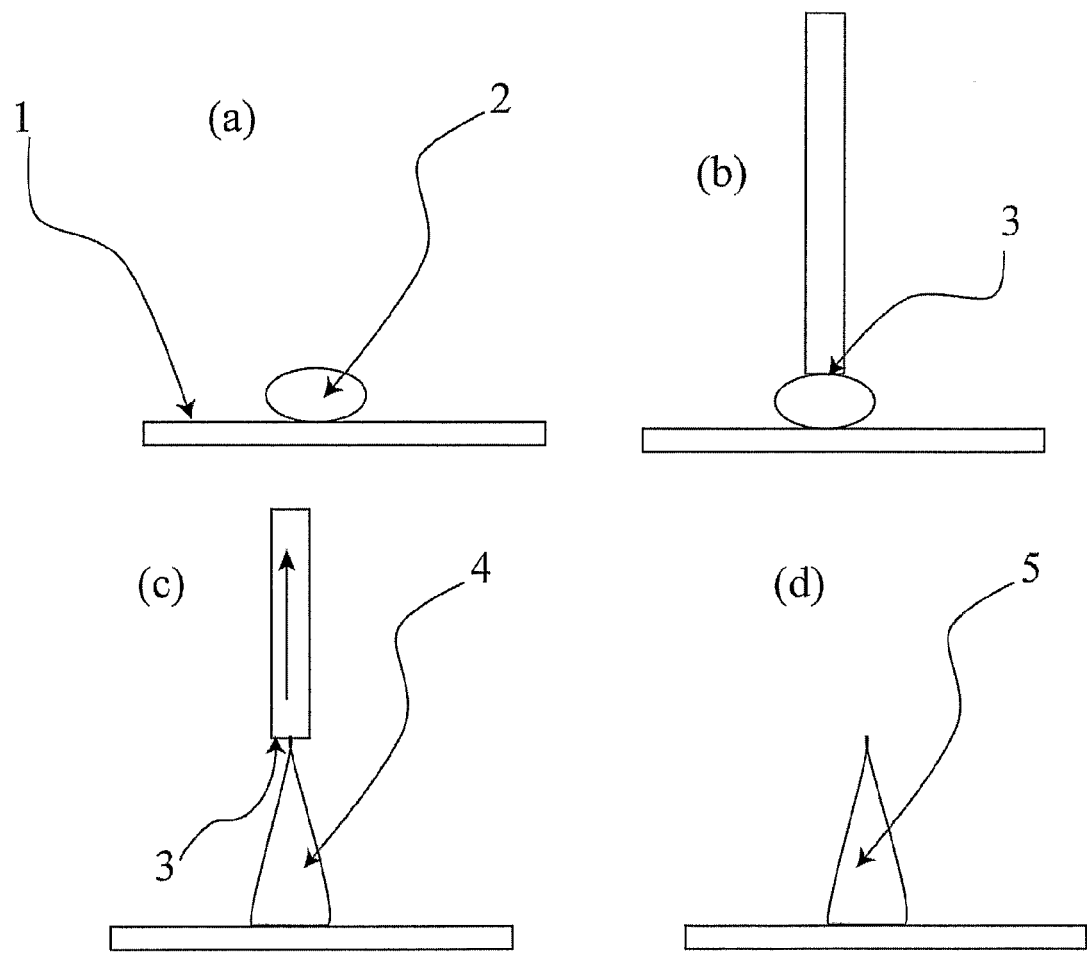
FIG. 1 shows a first embodiment of the present invention involving the drawing of a microneedle from non-solid material.

A first embodiment of the method of the present invention is now described with reference to FIG. 1. Referring to FIG. 1a, a droplet 2 of liquid is dispensed onto a first surface 1 onto which it is intended to form microneedles. The droplet 2 is preferably dispensed by an automated liquid handling means. A second surface 3 for producing a needle-like shape is brought-up to the droplet 2, so the second surface 3 is touching the surface of the droplet 2. The second surface in this case is a solid surface, although a liquid surface could be used, for example a liquid surface formed by a liquid disposed on the end of a solid rod or needle. The second surface 3 is then moved away from first surface 1, drawing the liquid droplet 2 into a needle shape 4. The liquid is caused to cure or otherwise solidify into a microneedle 5 and the second surface 3 is then removed.

The second surface 3 may be removed before curing or solidification has taken place, or even during the curing or solidification process. Removal of the second surface during curing or solidification may result in particularly sharp needles.

As an alternative to introducing the second surface 3 to the droplet 2 deposited on the first surface 1, the second surface 3 may be provided with the liquid and the liquid brought into contact with the first surface 1. Alternatively, the second surface 3 may be brought into proximity with the first surface 1 and the liquid dispensed so as to form contact with the first surface and the second surface. This may be affected by providing a bore associated with the second surface and dispensing the liquid through the bore.

Relative movement of the first surface 1 and second surface 3 is important and therefore the position of the second surface 3 may be fixed, with the first surface 1 being moved in order to bring the second surface 3 into contact with the droplet 2.

The needle-like shape may be solidified by cooling or by curing. This may be performed, for example, by using a curable liquid, such as a UV-curable acrylate adhesive, and by exposing the liquid to UV light to cure the adhesive. The liquid may be an epoxy resin. In this case, the first surface may be moved relative to the second surface to produce an elongate structure. This elongate structure is allowed to solidify over time. The elongate structure is then severed to allow the second surface to be removed from the first surface. This severing action causes the formation of a needle-like structure on the first surface.

Figure 2:
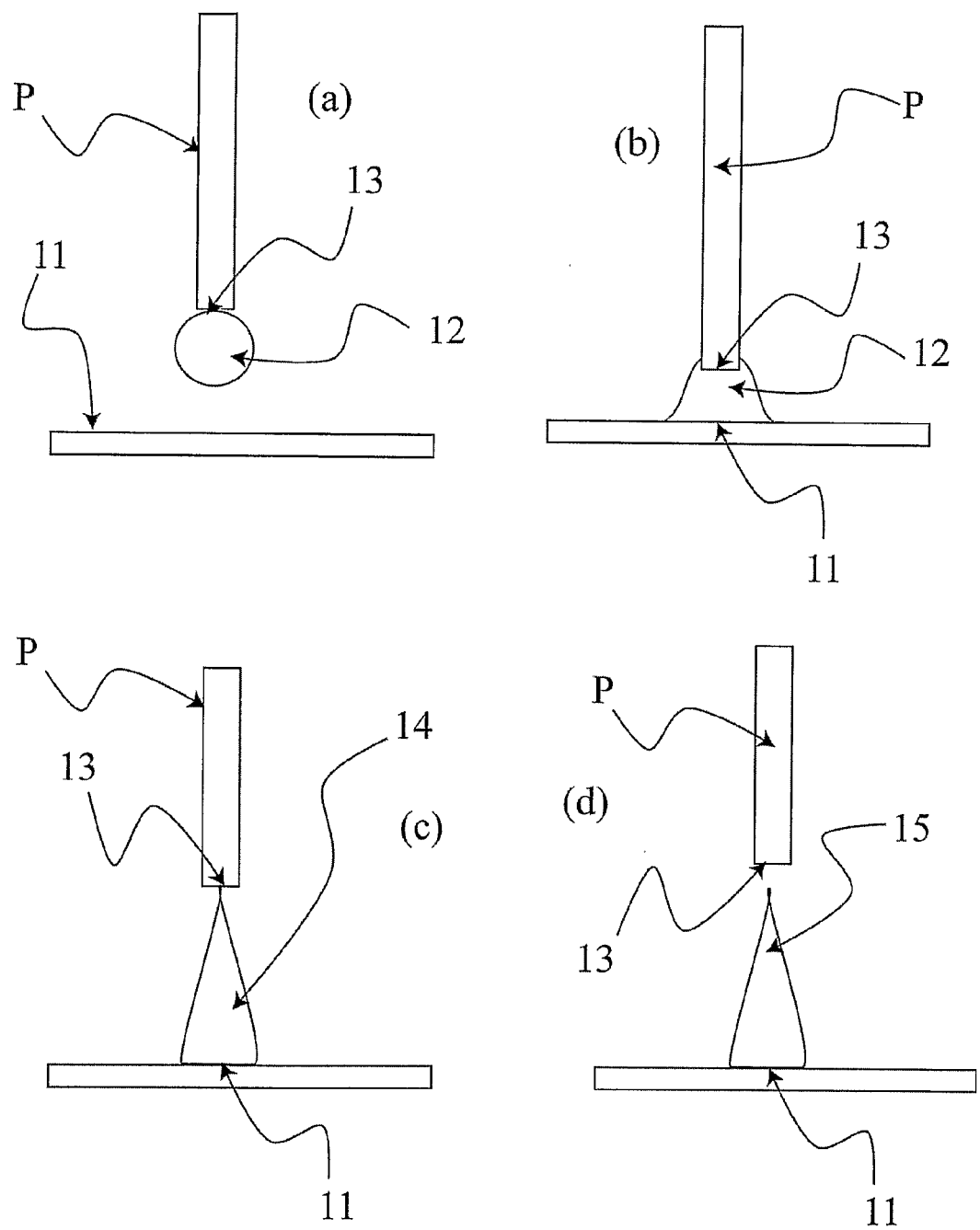
FIG. 2 shows a second embodiment of the present invention involving the drawing of a microneedle from non-solid material.

A second example of the invention is now described with reference to FIG. 2. A spotting device such as a microarrayer may be used to place the liquid on a surface to act as a reservoir. A pin P of diameter 0.4 mm was attached point downwards to a non-mobile support. A reservoir of non-solid substance from which the microneedle was to be made (in this case, a large spot of commercially available UV curing acrylate adhesive) was moved on a translation stage so that the head of the pin P was immersed in the substance for three seconds to produce a droplet of liquid 12 in contact with the end of the pin P. The solid surface 11 onto which the microneedle was to be formed was moved towards the second surface 13 (provided by the pin P) until the liquid 12 present on the end of the pin touched the solid surface 11. The solid surface 11 is allowed to touch the liquid-covered pin in such a way as to allow the liquid 12 to form a spot (see (b)). A UV source (a UV light emitting diode, not shown) supplies UV radiation to cure liquid 12. During curing, the solid surface 11 is moved away from the second surface 13 in a controlled manner using the translation stage to produce a needle-like shape 14 (see (c)). After curing, the finished needle 15 is left on the surface 1 (see (d)). This process produced a sharp needle structure of approximately 400 micrometers in height.

Needles were produced using a variety of solid surfaces, including paper, glass, plastic, a transdermal drug delivery patch, an adhesive semipermeable dressing film, and the adhesive side of pressure sensitive adhesive tape. Use of pins of a larger diameter enabled the production of sharp needles of height over 1 mm. Pins of a smaller diameter enabled production of structures of 250 µm in height.

A third example of the method of the present invention is now described. Spots of a viscous epoxy resin were dispensed on a first glass surface using contact printing. The first glass surface was then placed on a stage moveable in the z direction. The first glass surface was approximated to a second, fixed glass-surface, such that the drops of epoxy resin were touching the second glass surface. The first and second glass surfaces were slowly moved apart during curing of the resin, such that needle structures were drawn from each surface. After 3 hours, the resin had solidified, and any remaining connecting strands between the two surfaces were severed with scissors. The result was two glass surfaces with very sharp, hard microneedle structures projecting perpendicular to the surface. During curing, the tips of the needles were easy to bend, and could be deflected into curved, or even hooked structures. Loops could also be formed by pressing the flexible tips against the glass surface. These shapes persisted after curing was completed.

In the examples above, the second surface may have a low surface area for contact with the liquid. This enables fine, needle-like structures to be produced. The second surface may be provided by the tip of a pointed object such as a pin, typically having a diameter of 0.4 mm.

The second surface may remain in needle-drawing contact with the liquid by virtue of the surface properties of the liquid and second surface. This may be achieved, for example, by using an adhesive as the liquid. Alternatively, the second surface may be held in contact with the liquid by use of a vacuum with the second surface. Alternatively, the second surface may be provided by a structure provided with a bore into which the liquid may flow by virtue of capillary action.

The method may further comprise moving the first surface relative to the second surface prior to solidification or curing so as to form a needle structure that is one or more of curved or inclined relative to the first surface or hook-bearing.

Figure 3:
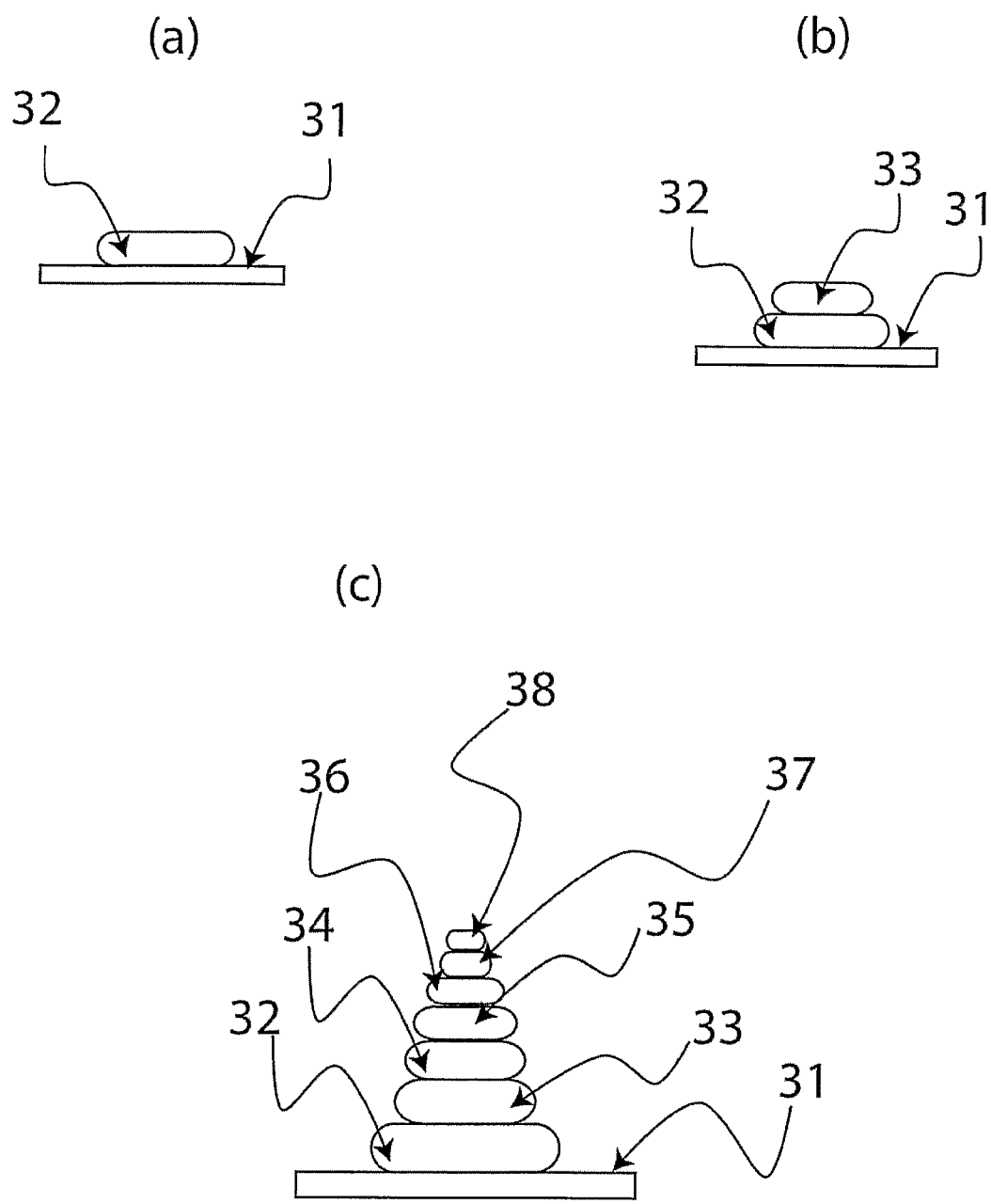
FIG. 3 shows a third embodiment of the present invention involving the sequential deposition of droplets of non-solid material to form a microneedle.

The previous three examples used a method of moving two surfaces apart to draw-out a needle shape. Printing methods such as stencil deposition or contact printing can be used to deposit drops of various sizes, or the same sizes of material on top of each other, in order to produce a needle-like shape. An example of such a method is now described with reference to FIG. 3. Referring to FIG. 3, a first portion 32 of non-solid substance in the form of a UV curable adhesive is deposited onto a first surface 31 using an automated liquid handling system (not shown) (see (a)).

The substance is then cured or at least partially cured using a UV light source (not shown). A second portion 33 is then deposited onto the first portion 32 of substance, and is subsequently cured as previously described (see (b)). This process is repeated until several portions 32, 33, 34, 35, 36, 37 and 38 are deposited one on top of another (see (c)). The volume of each portion is less than that of the immediately underlying portion. In this way, a conical or needle-like solid structure may be built.

Figure 4:
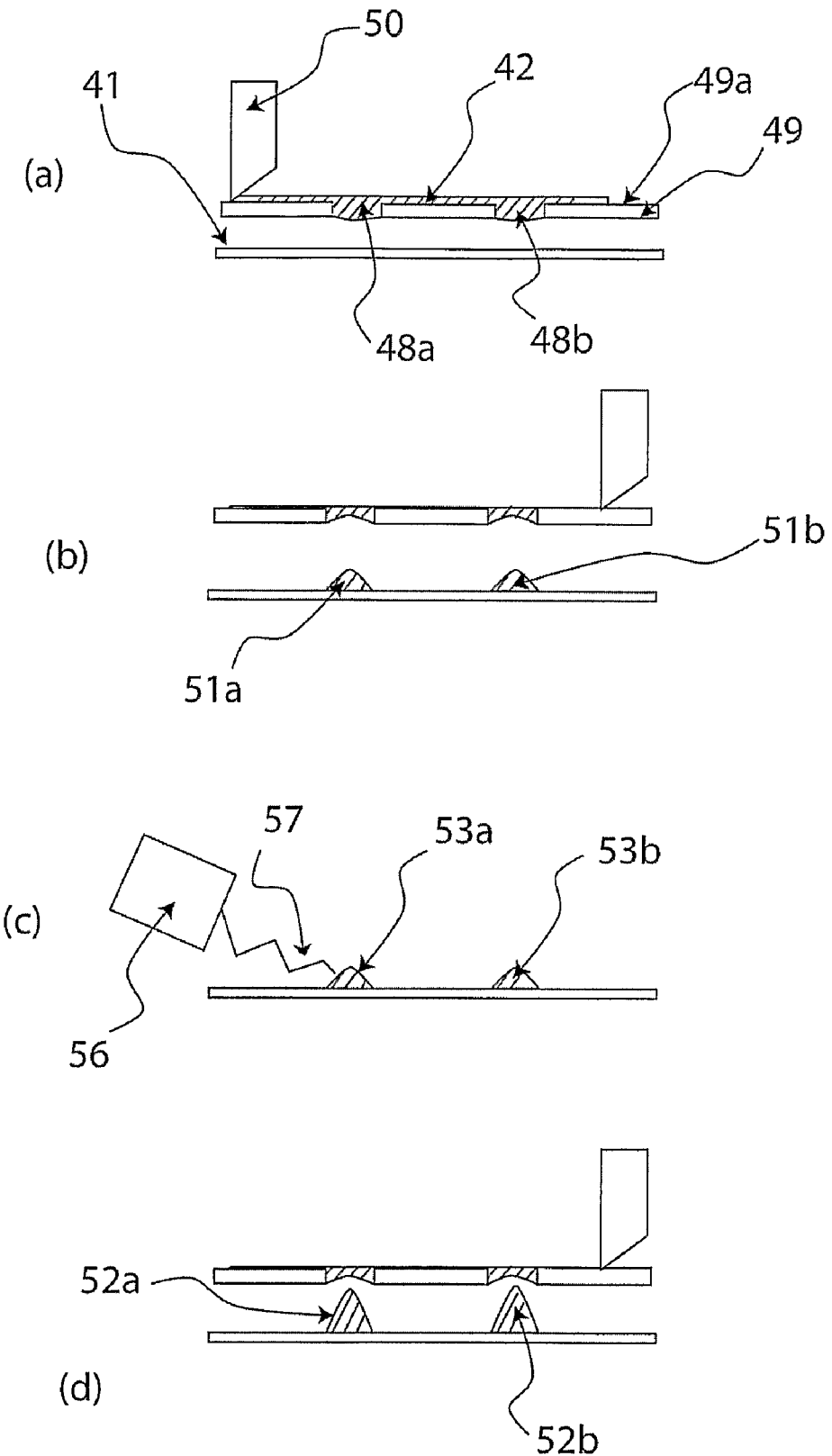
FIG. 4 shows a fourth embodiment of the present invention involving the use of a stencil to sequentially deposit droplets of non-solid material on top of each other to form a microneedle.

A further embodiment of a method of producing needle-like shapes by the sequential deposition of portions of substance is now described with reference to FIG. 4. A stencil 49 is brought into proximity to a first surface 41 (see FIG. 4a) The first surface 41 is provided by the upper surface of a flexible substrate. The stencil 49 is provided with approximately 1000 apertures, each of 100 µm diameter, in a 1 cm² area. Only two of the apertures, 48a and 48b, are shown here for clarity. A non-solid substance, in this case a UV-curable acrylate 42, was deposited onto the upper surface 49a of stencil 49 using a squeegee 50 which was wiped over upper surface 49a. This wiping action urged the acrylate 42 into the apertures 48a and 48b and urges stencil 49 into contact with the first surface 41. The acrylate 42 adheres to the first surface 41 so that when the stencil 49 is moved away from the first surface 41 (see FIG. 4b), portions 51a, 51b of acrylate remain on the first surface 41. The portions of acrylate 51a, 51b are then cured by exposure to UV radiation (shown schematically as 57) emitted from a UV "spot" source 56 (FIG. 4c) to form solid structures 53a, 53b. The stencil 49 was replaced so that further portions of non-solid substance 42 could be deposited onto the existing structures 53a, 53b. The steps as described with reference to FIGS. 4a, 4b and 4c were further repeated to form an array of needle-like shapes 52a, 52b of approximately 0.7 mm height and having a tip diameter of approximately 20 µm. Needle arrays produced by this method were shown to be capable of penetration of human stratum corneum in vitro.

Using this technique, height of the needles can be increased to any size, and the tip diameter can be varied by changing variables such as material rheology, aperture size and squeegie speed or movement in the z axis.

The sequential deposition technique described above with reference to FIGS. 3 and 4 may be combined with a needle-drawing methodology as described previously. Such techniques can also be used to produce needles of varied composition, for instance with one type of material forming a rod or other structure inside a needle of different composition. The internal structure may be formed from a porous material, or may be dissolvable to allow a pathway through the microneedle.

The invention claimed is:

1. A method of manufacturing a microneedle or microimplant, the method comprising:
    (i) depositing a first portion or droplet of substance onto a first surface; and
    (ii) forming a solid needle from the substance, wherein step (ii) comprises sequentially depositing a plurality of portions or droplets of substance onto the first portion or droplet of substance.

2. A method according to claim 1 wherein the volume of a portion or droplet is smaller than the volume of the immediately underlying portion or droplet.

3. A method according to claim 1 wherein step (ii) comprises sequentially depositing a plurality of portions or droplets of substance in non-solid form, each portion or droplet being at least partially solidified prior to the deposition of a further portion or droplet of substance in non-solid form thereon.

4. A method according to claim 1 wherein the depositing of the substance is performed by printing.

5. A method according to claim 1 wherein step (i) comprises providing a stencil having at least one aperture, and depositing the substance through the at least one aperture onto the first surface.

6. A method according to claim 5 wherein depositing the substance through the at least one aperture onto the first substrate is achieved by urging the substance into the at least one aperture.

7. A method according to claim 5 wherein step (ii) comprises sequentially depositing a plurality of portions or droplets of substance through the at least one aperture of the stencil.

8. A method according to claim 7 wherein at least one portion or droplet is deposited in non-solid form, the said at least one portion or droplet being at least partially solidified prior to the deposition of a further portion or droplet of substance thereon.

9. A method according to claim 1 wherein the solid needle comprises a material selected from the group consisting of an organic polymer, a silicone polymer, a metal, a mixture of a metal with non-metal materials and silica.

10. A method according to claim 1, comprising the formation of an array of microneedles, the method comprising:
    i) depositing an array of first portions or droplets of substance onto a first surface; and
    ii) forming an array of solid needles from the substance, wherein step (ii) comprises depositing a plurality of portions or droplets of substance onto each of the first portions or droplets of substance.

11. A method of manufacturing a microneedle or microimplant, the method comprising:

i) depositing a substance onto a first surface; and (ii) forming a solid needle from the substance, wherein step (i) comprises providing a stencil having at least one aperture, and depositing the substance through the at least one aperture onto the first surface.

12. A method according to claim 11 wherein depositing the substance through the at least one aperture onto the first substrate is achieved by urging the substance into the at least one aperture.

13. A method according to claim 11 wherein step (ii) comprises moving the stencil in relation to the first surface, thus forming a needle-like shape.

14. A method according to claim 11 wherein step (ii) comprises sequentially depositing a plurality of portions or droplets of substance through the at least one aperture of the stencil.

15. A method according to claim 14 wherein at least one portion or droplet is deposited in non-solid form, the at least one portion or droplet being at least partially solidified prior to the deposition of a further portion or droplet of substance thereon.

16. A method of manufacturing a microneedle or microimplant, the method comprising:

(i) depositing a first portion or droplet of substance onto a first surface; and (ii) forming a solid needle from the substance, (iii) wherein step (ii) comprises depositing a second portion or droplet of substance onto the first portion or droplet of substance, wherein the depositing of the substance is performed by printing.

\* \* \* \* \*

UNITED STATES PATENT AND TRADEMARK OFFICE
CERTIFICATE OF CORRECTION

PATENT NO. : 8,192,787 B2
APPLICATION NO. : 11/660341
DATED : June 5, 2012
INVENTOR(S) : Kirby Page 1 of 1

It is certified that error appears in the above-identified patent and that said Letters Patent is hereby corrected as shown below:

Front page, (73) Assignee: "Innoture Limited, Cardiff (GB)" should read --Innoture IP Limited, London (GB)--

Signed and Sealed this
Twelfth Day of February, 2013

Teresa Stanek Rea
*Acting Director of the United States Patent and Trademark Office*